(12) United States Patent
Hoftman

(10) Patent No.: US 6,607,170 B1
(45) Date of Patent: Aug. 19, 2003

(54) SAFE DISPOSAL OF SURGICAL SPONGES

(76) Inventor: Moshe Hoftman, 22205 Daedenne Ave., Calabasas, CA (US) 91302

( * ) Notice: Subject to any disclaimer, the term of this patent is extended or adjusted under 35 U.S.C. 154(b) by 0 days.

(21) Appl. No.: 08/810,192

(22) Filed: Mar. 3, 1997

Related U.S. Application Data

(63) Continuation-in-part of application No. 08/404,285, filed on Mar. 14, 1995, now Pat. No. 5,658,077, which is a continuation-in-part of application No. 08/204,674, filed on Mar. 2, 1994, now abandoned.

(51) Int. Cl.$^7$ ................................................ A47K 1/04
(52) U.S. Cl. ................... 248/129; 248/129; 248/125.1; 206/370
(58) Field of Search ............................ 248/95, 98, 146, 248/150, 1, 155, 156, 129, 125.1, 125.8; 206/438, 806, 370, 527, 362

(56) References Cited

U.S. PATENT DOCUMENTS

| | | | | |
|---|---|---|---|---|
| 1,423,612 A | * | 7/1922 | Jewett | 211/85.31 |
| 1,799,079 A | * | 3/1931 | Bemis | 248/146 |
| 3,324,483 A | * | 6/1967 | Conroy | 4/638 |
| 4,096,951 A | * | 6/1978 | Menssen | 211/207 |
| 4,234,086 A | * | 11/1980 | Dorton | 206/362 |
| 4,429,789 A | * | 2/1984 | Puckett, Jr. | 206/370 |
| 4,497,077 A | * | 2/1985 | Provost | 4/628 |
| 4,713,136 A | * | 12/1987 | Li | 156/229 |
| 4,884,360 A | * | 12/1989 | Pearcy | 43/54.1 |
| 5,048,683 A | * | 9/1991 | Westlake | 206/362 |
| 5,288,093 A | * | 2/1994 | Gross | 280/292 |
| 5,337,992 A | * | 8/1994 | Pryor et al. | 245/125.1 |
| 5,658,077 A | * | 8/1997 | Hoftman | 383/35 |

* cited by examiner

Primary Examiner—Leslie A. Braun
Assistant Examiner—Gwendolyn Baxter

(57) ABSTRACT

A bag member for receiving used surgical sponges in a surgical sponge storing system, composed of a first sheet of flexible material forming a main bag having a periphery, and a plurality of second bag members mounted to the first sheet and forming sponge holding bags. A surgical sponge storage and counting system for use in a surgical operating room, composed of: a pail; a stand mounted on wheels for permitting the stand to be rolled across an operating room floor; a pail supporting member for supporting the pail; a unit for mounting the pail supporting member on the stand and for adjusting the height of the pail above the floor; and a bag member receivable in the pail for containing and storing used surgical sponges.

4 Claims, 4 Drawing Sheets

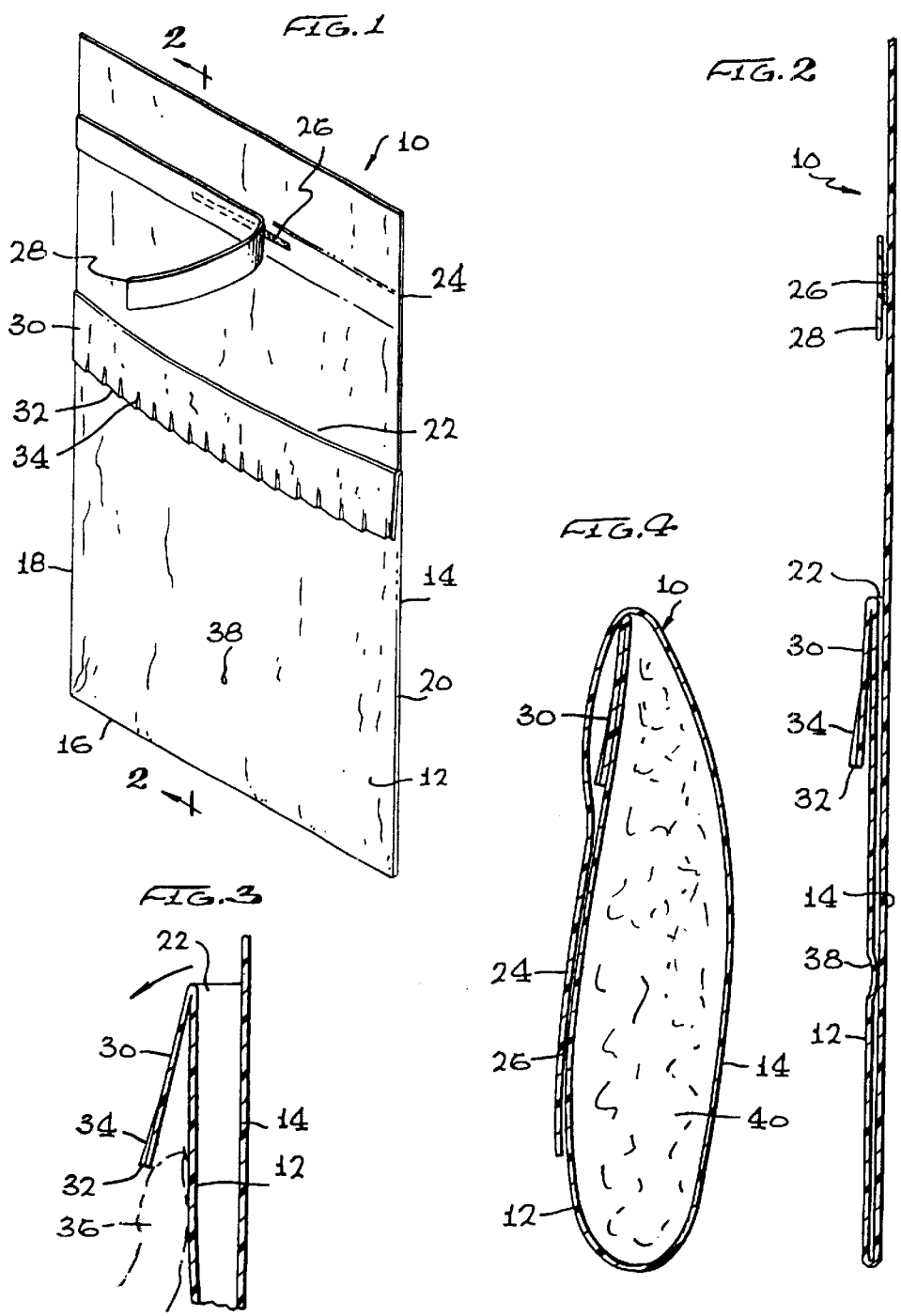

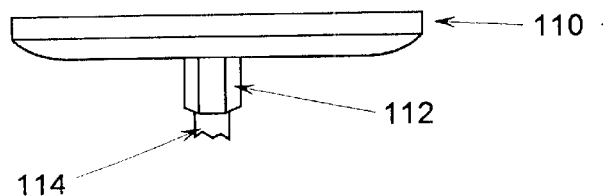
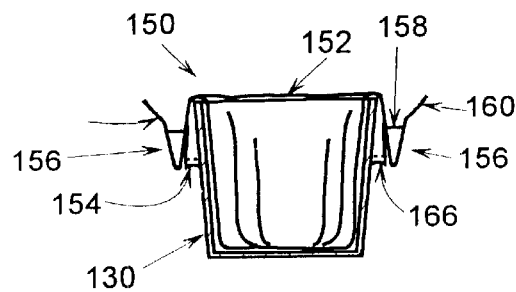
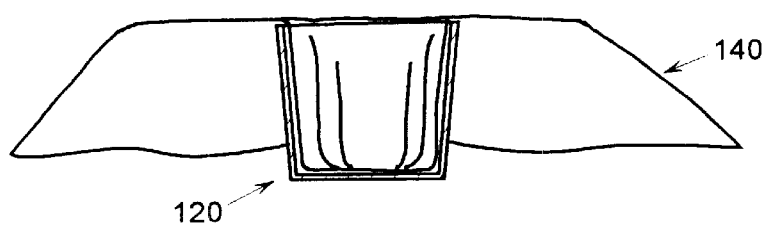
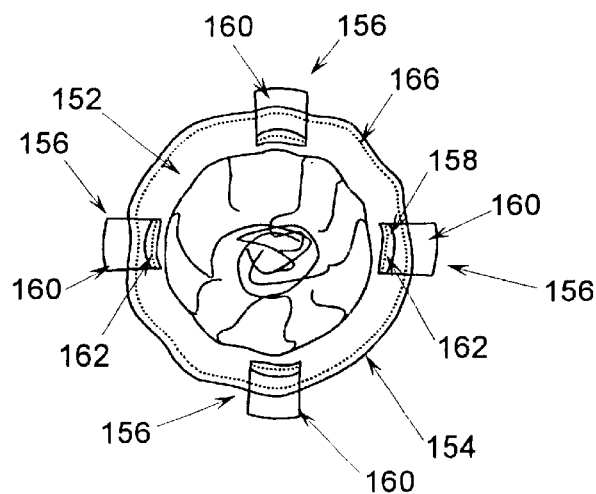

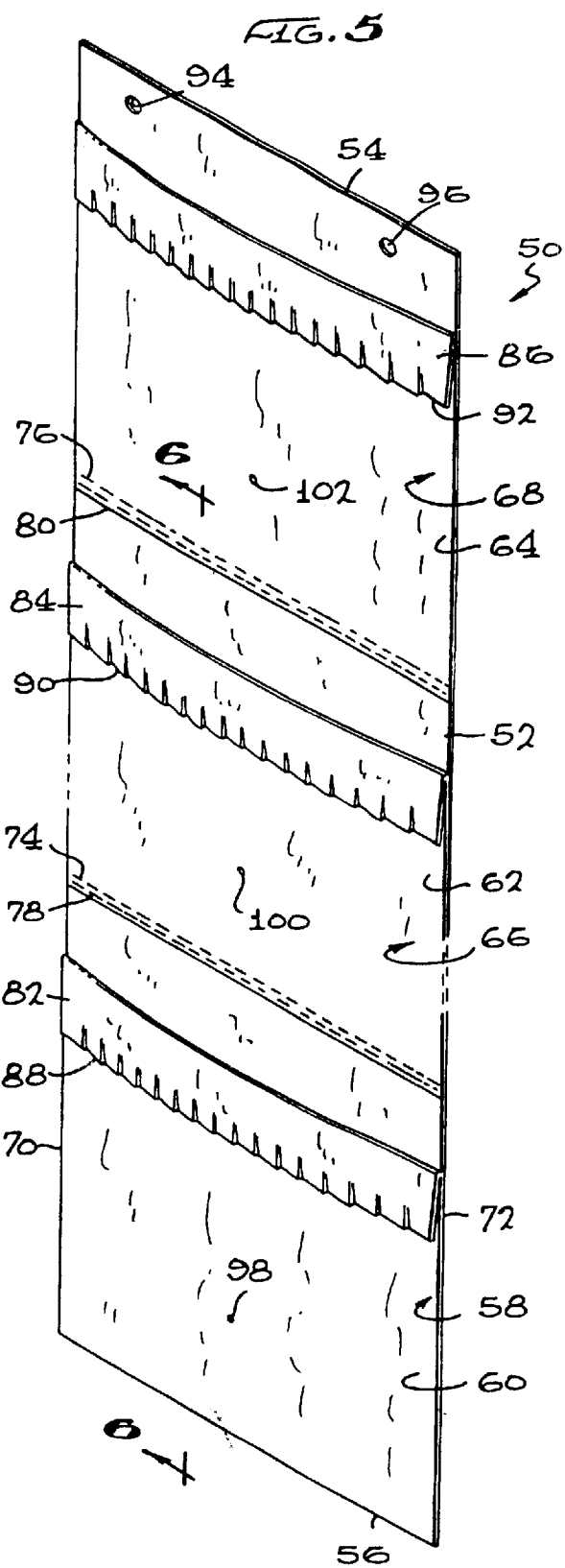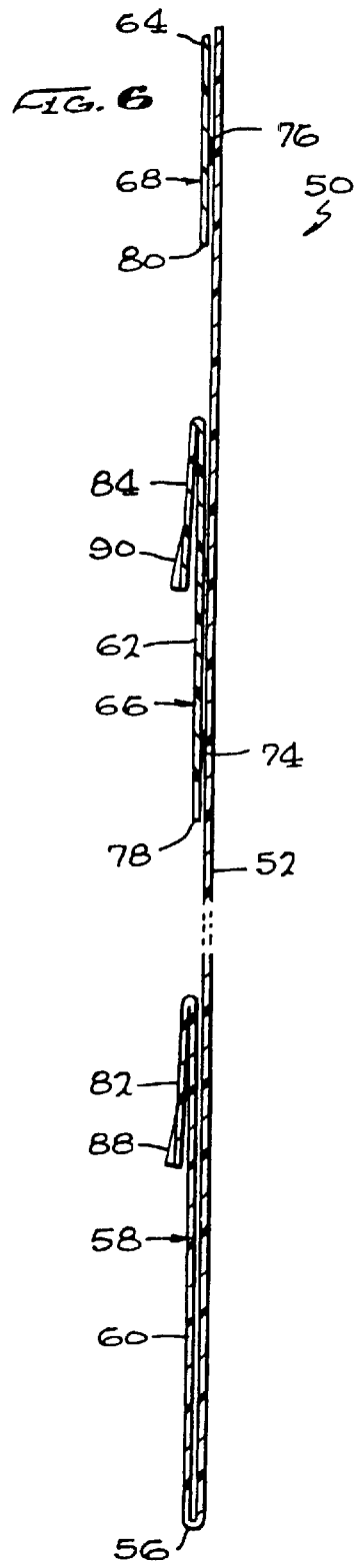

SAFE DISPOSAL OF SURGICAL SPONGES

This application is a continuation in part of patent application Ser. No. 08/404,285 filed Mar. 14, 1995 now U.S. Pat. No. 5,658,077, which is a continuation in part of patent application Ser. No. 08/204,674, filed Mar. 2, 1994, abandoned.

BACKGROUND OF THE INVENTION

The present invention relates to the disposal of surgical sponges.

Surgical procedures frequently involve the use of sponges, sometimes referred to as swabs, to absorb blood and other body fluids at the operating field, for example to permit unobstructed viewing of the region being operated upon. Before completion of the surgical procedure, all of the sponges which have been introduced into the patient's body must have been removed. This requires that personnel in the operating room keep track of the number of sponges which have been placed in the patient's body, and the number of sponges subsequently removed therefrom.

Standard procedures which have been developed for this purpose include those in which used sponges which have been removed from the patient's body during surgery are counted in groups of a given number, typically five or ten sponges to a group, each counted group is placed in a container, such as a plastic bag, and before the surgical procedure has been completed, typically by suturing the incisions made during surgery, all groups of used sponges are counted to verify that all sponges which have been used are accounted for.

After a sponge has been withdrawn from the patient, it is common practice to drop or throw the sponge into a bucket, known in the art as a kick bucket, which rests on the floor at a location selected so as not to interfere with the surgical procedure. A kick bucket is typically a bucket mounted on wheels to be easily moved across the operating room floor. Buckets of this type are marketed by various companies, including Vollrath Group Inc., Gallaway, Tenn. 38036 and Blickman Health Industries, Inc., Fairlawn, N.J. 07410.

At various times during an operation, sponges will be transferred from the bucket to a storage and disposal unit constructed to permit a count of used sponges to be maintained.

One commercially available disposal system consists simply of a set of clear plastic bags each of which is intended to store five sponges of one type, such as laparotomy sponges, or ten sponges of another type, such as raytex sponges. After the given number of sponges has been placed in the bag, it is closed. The bag is transparent, so that the sponges remain visible for observation by attending physicians. Bags of this type are distributed, for example, by Sage Products Inc. of Crystal Lake, Ill. 60014.

Another commercially available system is composed of a clear plastic component provided with a plurality of pockets. Either five or ten sponges, depending on the type, can be counted into each pocket. Here again, the sponges remain visible and, at the completion of surgery, the number of pockets which have been filled with sponges can be counted to produce a sponge count. Products of this type are marketed by, for example, Kendall Healthcare Products Company, under the trade name Curity", as well as by the above-identified Sage Products Inc.

The known systems described above have a number of drawbacks. For example, because available kick buckets generally rest on the floor, it is not possible for the operating room personnel to reliably drop or toss the sponges into the kick bucket. As a result, it frequently occurs that a certain number of used sponges, contaminated with blood, will be dropped onto the operating room floor, splashing blood-borne pathogens on the operating room floor, and must then be picked up by operating room personnel.

Then, the kick bucket must be displaced to the location where they are to be counted into bags or pockets and the person collecting the sponges must repeatedly bend over to pick up the sponges.

Thus, overall, the sponges must be subjected to a considerable amount of handling after use, with the risk of contamination of operating room personnel increasing with the amount of handling required.

SUMMARY OF THE INVENTION

It is an object of the present invention to provide a bag member for receiving used surgical sponges and a surgical sponge storage and counting system employing such bag members which eliminate or minimize the drawbacks encountered in the prior art.

A more specific object of the invention is to reduce the number of handling procedures required to transfer a used sponge from the patient to a location for final counting, containment and disposal.

Another object of the invention is to reduce the number of occasions on which a sponge will be dropped on the floor or blood from the sponge will drip on the floor of the operating room.

Another object of the invention is to reduce the physical demands imposed on operating room personnel in connection with disposal of used sponges.

Yet another specific object of the invention is to facilitate the transfer of used sponges to individual counting bags, or pockets, followed by sealing of the bags for final disposal.

The above and other objects are achieved, according to the present invention, by a bag member for receiving used surgical sponges in a surgical sponge storing system, comprising: a first sheet of flexible material forming a main bag having a periphery, and a plurality of second bag members mounted to the first sheet and forming sponge holding bags.

The objects according to the invention are further achieved by a surgical sponge storage and counting system for use in a surgical operating room, comprising: a pail; a stand mounted on wheels for permitting the stand to be rolled across an operating room floor; a pail supporting member for supporting the pail; means for mounting the pail supporting member on the stand and for adjusting the height of the pail above the floor; and a bag member as described above, receivable in the pail for containing and storing used surgical sponges.

In order to aid in the understanding of this invention, it can be stated in essentially summary form that it is directed to a sponge counting bag which is formed of front and back sheets of substantially transparent synthetic polymer composition material. The front and back sheets are closed at the bottom and side edges. The back sheet extends upward, and the front sheet is folded down at its top edge to form a cuff. The cuff is wrinkled on its free edge to permit easy opening of the bag. The sponge counting bag may have a reopenable, fold-down flap or may have a plurality of such bags arranged one above the other.

It is thus a purpose and advantage of this invention to provide a sponge counting bag which is easy to open so that sponges can be readily placed therein at the end of a surgical procedure so that they may be readily counted.

It is a further object and advantage of this invention to provide a sponge counting bag which facilitates placement of the sponges in the counting bag for subsequent counting by having a cuff thereon which is readily grasped or single-finger manipulated to pull the bag open.

It is a further purpose and advantage of this invention to provide a flap on the sponge counting bag which can releaseably close the bag.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1B is an elevational view of one of the components of the apparatus shown in FIG. 1A.

FIG. 1C is, an elevational, cross-sectional view showing portions of the apparatus of FIG. 1A associated with a bag member according to the invention and an additional plastic liner.

FIG. 1D is a plan view of the bag member shown in FIG. 1C.

FIG. 1 is an isometric view of the first preferred embodiment of the sponge counting bag of this invention.

FIG. 2 is an enlarged section taken generally along line 2—2 of FIG. 5.

FIG. 3 is an enlarged section of a portion of the bag shown in FIG. 2 showing the easy manipulation of the wrinkled edge.

FIG. 4 is a section similar to FIG. 2 showing the bag filled with sponges and showing its flap closed.

FIG. 5 is an isometric view of the second preferred embodiment of the sponge counting bag this invention, with parts broken away.

FIG. 6 is an enlarged section taken generally along the line 6—6 of FIG. 5, with parts broken away.

DESCRIPTION OF THE PREFERRED EMBODIMENTS

Figure 1A:
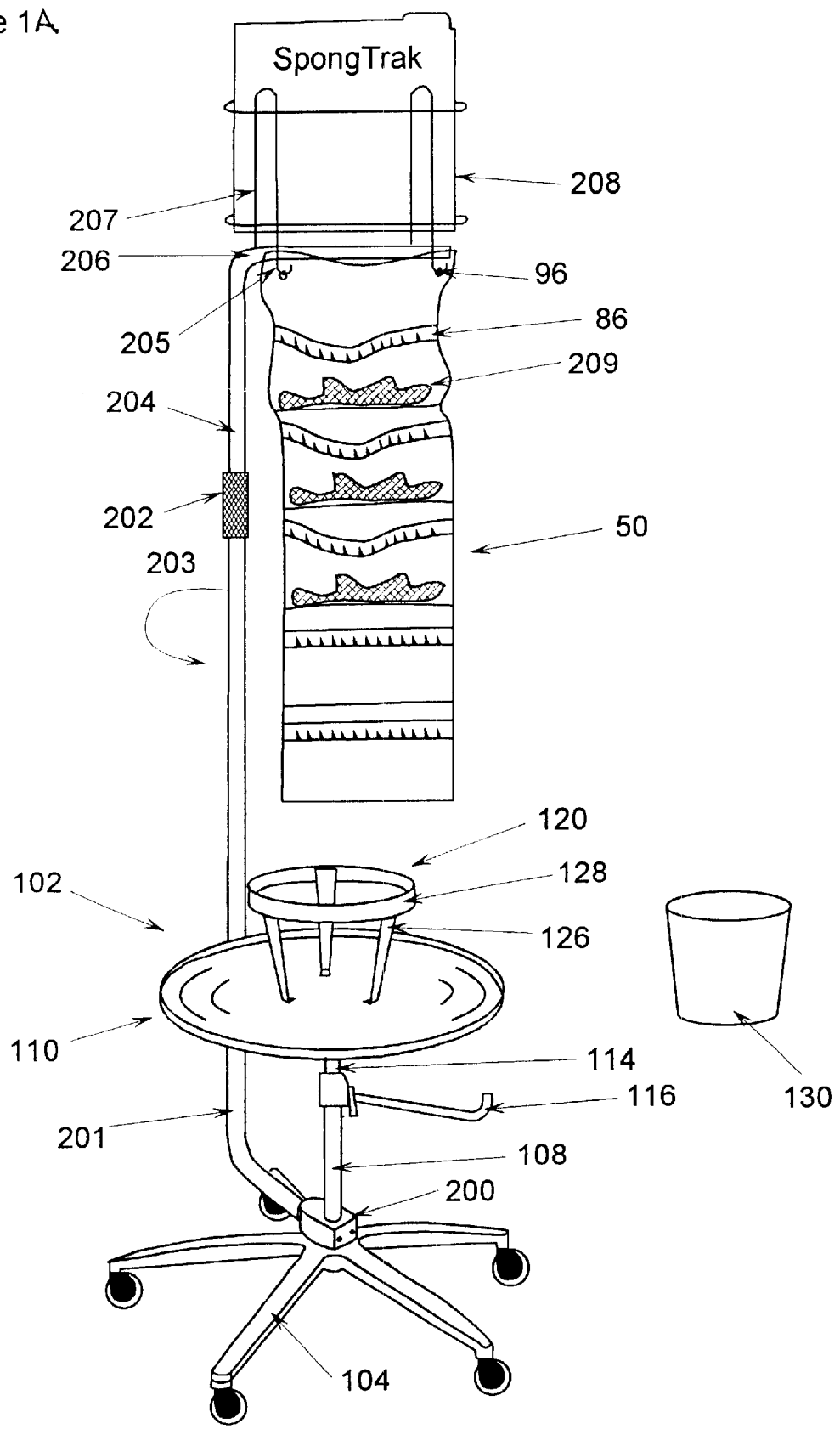
FIG. 1A is a perspective, partly exploded, view of an embodiment of a surgical sponge hold apparatus according to the invention.

FIG. 1A shows one embodiment of apparatus according to the invention which can be employed for initial collection of used surgical sponges during the course of a surgical procedure. This apparatus includes a stand 102 composed of a base 104 whose legs are provided-with casters 106 and an upright 108 extending vertically from base 104. Upright 108 preferably is a hollow tubular member.

Mounted above base 104 is a catch basin 110 provided at the center of its bottom nut 112 for receiving a threaded rod 114. Rod 114 extends into tubular upright 108 and is engaged by a locking, or latching, member 116 which is constructed to be manually operable in order to allow rod 114, and thus basin 110, to be moved vertically to a desired height above the operating room floor. When basin 110 is at the desired height, locking member 116 is released to automatically hold rod 114 in place with respect to upright 108. Locking member 116 can be of any known type which locks cooperating members in position when released.

The top surface of basin 110 carries a pail supporting member 120 composed of a plurality of flat bands 126 bent to have substantially an L shape with a short horizontal leg and a long upright leg, and a ring 128. The short legs of bands 126 are welded to basin 110 and the tops of the long legs of bands 126 are welded to ring 128. The components of supporting member 120 are shaped to provide a conforming receptacle for a pail 130.

Nut 112 may be welded to basin 110 and rod 114 is secured into nut 112. Thus, rod 114 is easily removable from basin 110 for cleaning.

With the apparatus illustrated in FIGS. 1A and 1B, the height of bucket 130 above the floor of the operating room can be readily adjusted over a given range to a height which is most convenient for the operating room personnel responsible for transferring used sponges to, and subsequently removing used sponges from, bucket 130. At the same time, the advantages of conventional kick buckets, i.e. their ability to be easily rolled to any desired location in the operating room, is maintained.

If, during use, it should be found that bucket 130 has not been placed at the most convenient height, its height can be readily adjusted by actuating locking member 116, manually raising basin 110 or supporting member 120 and releasing locking member 116 when pail 130 is at the desired height.

The height adjustable kick bucket illustrated in FIGS. 1A and 1B can be employed in accordance with conventional practice in the art, i.e. used sponges can be dropped or placed in a liner in pail 130, and the sponges can then be counted for subsequent disposal.

However, according to a further feature of the invention, the system shown in FIG. 1A may be supplemented by a novel plastic bag member according to the invention, as shown in FIGS. 1C and 1D. FIG. 1C illustrates pail supporting member 120 and pail 130 of the device shown in FIGS. 1A and 1B. As illustrated in FIG. 1C, there may be provided, between pail supporting member 120 and pail 130, a lining sheet 140 made of any suitable nonporous plastic material which will overlie, and act as a liner for, the interior of basin 110. Then, pail 130 is placed in supporting member 120 with sheet 140 interposed therebetween.

According to the invention, bag member 150 is constituted by a sheet 152 of nonporous plastic material, which may be any material acceptable for storage and disposal of infectious waste, such as used surgical sponges. Sheet 152 is configured to have the form of a bag with a periphery, or outer edge, 154. Thus, sheet 152 can be installed to serve as a liner for the interior of pail 130.

In further accordance with this aspect of the invention, sheet 152 carries a plurality of sponge holding bags 156 each having an open end 158 for receiving used sponges. The side of each bag 156 which is remote from sheet 152 is given a sufficient length to provide a flap 160 which can be gripped at a safe distance from the bag opening provides a guide surface for safely directing sponges into the bag and can be folded into the associated open end 158 in order to loosely close the associated bag 156.

Each bag 156 may be bonded, as by cementing or heat sealing, to sheet 152, for example along a line 162 adjacent the associated open end 158.

It will be noted that in the embodiment illustrated in FIGS. 1C and 1D, sponge holding bags 156 are oriented such that their open ends 158 face away from edge 154 of sheet 152 and toward the interior, or center, of the bag formed by sheet 152. With this orientation, as is apparent from a consideration of FIGS. 1C and 1D, when bag member 150 is inserted into pail 30, the peripheral portion of bag member 150, or sheet 152, is draped over the edge of pail 130 so that the open ends 158 of sponge holding bags 156 are oriented upwardly, in the normal position for receiving items.

Thus, in the use of bag member 150, during the course of an operation, used sponges will be placed in the portion of bag member 150 which lines the interior of pail 130. At any time during the surgical procedure, when a sufficient number of used sponges have accumulated, the sponges can be counted into sponge holding bags 156 and after the predetermined number of sponges has been counted into a bag 156, flap 160 may be folded over into opening 158 so as to enclose the sponges therein and thus loosely close the associated bag.

The opposing faces of each bag 156 are sealed together along a sealing line (not visible) which extends over a portion of the height of the bag from the bottom thereof to divide the interior of bag 156 into two halves. The manner in which this sealing line is employed will be described in detail below.

In accordance with the usual practice in this art, each bag 156 may be employed to receive five sponges of one type, such as laparotomy sponges, or ten sponges of a second type, such as raytex, sponges. In the former case, the operating room personnel may break the dividing seal in the associated bag 156, simply by pressing down on the seal with the first sponge introduced or with the hand before introducing the first sponge. In the case when ten sponges are to be stored in a bag 156, the dividing seal is left intact and five sponges are placed to each side of the dividing seal.

If the sponges being disposed of are the type equipped with string tabs, a portion of the string tab of each sponge may be allowed to hang outside the associated bag 156 when sponges are initially counted and introduced therein. Then, each string tab may be placed fully within the associated bag 156 at the time of a subsequent sponge count. After the appropriate number of sponges has been counted into a bag 156, and flap 160 has also been folded into bag 156, the number and type of sponges therein can be written on the bag with a suitable marker.

After all four bags 156 have been filled with the requisite number of sponges, and the count has been verified by any approved procedure, edge 154 of sheet 152 can be lifted in order to bring bags 156 to the interior of bag member 150. As this is being done, bags 156 will roll or flip over toward the interior and bottom of bag member 150. Then, to complete the sealing process, the edge of sheet 152 may be torn away along a perforation 166, providing a thin strip of plastic which can be used to tie the open end of bag member 150 closed. Bag member 150 is thin ready for final disposal.

The system according to the invention offers the further advantage of reducing the risks associated with airborne and blood borne pathogens because contaminated sponges are never removed from the apparatus until final disposal.

All of the parts of bag member 150 are preferably made of a material or materials which are nonpermeable, transparent and safely incinerable.

While the description above refers to particular embodiments of the present invention, it will be understood that many modifications may be made without departing from the spirit thereof. The accompanying claims are intended to cover such modifications as would fall within the true scope and spirit of the present invention.

Specific Embodiment of Sponge Counting Bags

The first preferred embodiment of the sponge counting bag of this invention is generally indicated at 10 in FIGS. 1, 2 and 4. The bag 10 is made of substantially transparent flexible synthetic polymer composition sheet material such as polyethylene. The bag has a front layer 12 and a back layer 14. These layers are attached together along bottom edge 16 and left and right edges 18 and 20 to create a bag having an opening 22 at its top. The back layer extends upward above the bag opening to form closure flap 24. The closure flap has a height almost as tall as the bag from its bottom edge to its opening so that the closure flap can be pulled down over the front for substantial overlap over the bag opening.

A line of pressure sensitive adhesive 26 is provided on the front of the flap 24. The line of adhesive is covered by protective release strip 28. The release strip 28 covers the adhesive 26 until adhesive closure of the bag is desired, whereupon the release strip is removed. It is shown half pulled off in FIG. 5. After it is removed, the flap is pulled down over the front of the bag and is attached closed by means of the pressure sensitive adhesive, as seen in FIG. 4. The adhesive is of such nature as to be sufficiently aggressive to securely hold down the closure flap to hold the bag closed under ordinary circumstances. However, the aggressiveness of the adhesive is sufficiently limited so that, if it is required that the bag be reopened, such can be accomplished without tearing the bag. After closure, if the closure flap is lifted, the bag can be opened without tearing.

Another important feature of the bag 10 is the folding down of the upper edge of the front layer to form folded-down flap or cuff 30. The cuff 30 is stretched along its lower edge 32 to form wrinkles 34. The wrinkles can be achieved by any convenient means such as by hot corrugated rollers or by direct application of heat, such as infrared or laser application. In this latter case of the application of heat, the polymer material is such that, when heat is applied, wrinkling occurs. Since there are wrinkles adjacent the lower edge of the cuff, this lower edge cannot lie directly flat against the front layer 12. As a consequence, a finger 36 can readily engage under the cuff 30 to pull open the opening 22 seen in FIG. 3. The wrinkling prevents the inconvenience and delay which sometimes occurs when two polymer layers must be separated.

The sponge counting bag 10 has a tack seal 38 between its front and back layers, see FIGS. 1 and 2. This tack seal is substantially midway between the left and right edges 18 and 20. The tack seal is about one-third the way up the bag 10 between its bottom edge 16 and opening 22. The tack seal is not a very localized one, but may be a ring to spread the sealing. The tack seal is configured so that it holds the front and back together moderately well but, when a larger bag volume is required, the tack seal can be pulled apart without making an opening in the front or back layers of the bag.

When the sponge counting bag 10 is in use, it is held up by the top edge of the closure flap 24 in the open position shown in FIGS. 1 and 2. When the sponges are small, the tack seal 38 is left attached. Five small sponges can be placed in an upright column on each side of the tack seal. Thus, the tack seal holds the columns of sponges in line for recounting even after the bag is closed. However, when the sponges are larger, larger bag volume is required so that the tack seal is pulled apart.

Sponges 40 are placed in the bag to a determined count until the bag is full, as seen in FIG. 4. When full, the release strip 28 is removed and the closure flap is pulled down and sealed. If a recount is necessary, just prior to closing of the operating incision by the surgeon, the sponges in the bag can be counted through the transparency thereof, or if there are several layers, the bag can be reopened by pulling open the flap so that the individual sponges can be separated, counted and replaced into the bag. This permits easy recounting and easy resealing.

A second preferred embodiment of the sponge counting bag of this invention is shown in FIGS. 5 and 6 where it is generally indicated at 50. The sponge counting bag 50 comprises a plurality of attached bags arranged one above the other. The sponge counting bag 50 comprises a back layer 52 of flexible substantially transparent, thermoplastic synthetic polymer composition material, such as polyethylene. In the original manufacture of the sponge counting bag 50, the back layer is folded up all the way to the back top edge 54. The bottom fold 56 closes the bottom of the lowermost sponge bag 58 of the upright string of sponge counting bags. The folding up of the back layer provides front layer 60, front layer 62, and front layer 64, respectively, of the lower sponge bag 58, the intermediate sponge bag 56 and the upper sponge bag 68. The three sponge bags illustrated are sealed at their left and right edges 70 and 72 by heat sealing. In addition, the lower closure of the intermediate and upper sponge bags 66 and 68 are formed by heat-sealing along heat seal bottom edge lines 74 and 76. The openings of the lower and intermediate bags 58 and 66 are created by slitting the front layer at slit lines 78 and 80. This creates flaps or cuffs 82 and 84. These cuffs are folded down, as shown. They may have to be separated at their edges for proper folding. The top edge of the front sheet is also folded down at the upper sponge bag to create flap or cuff 86. It may be necessary to reheat-seal the edges of these cuffs in order to hold them down, as shown. The cuffs are wrinkled along their lower, free edge. Wrinkles 88, 90 and 92 are shown. These wrinkles permit easy opening of each of the bags, as desired. The entire bag system 50 is retained in place by hanging it from convenient hooks which engage in support holes 94 and 96. The set of bags 50 also has tack seals, 98, 100 and 102 for the same purpose as the tack seal 38.

The system of sponge counting bags 50 is used in much the same manner as the use of the sponge counting bag 10. The system of bags 50 is supported from suitable hooks engaging in its support holes near the top edge. Each of the individual bags is then positioned for accessibility. When a used sponge is received, the nurse places it in one of the bags. This is accomplished by slipping a finger under the wrinkled edge which opens that bag without difficulty. This provides ease and speed of operation. The sponges in the bags are visible so that they may be counted at the end of the surgical procedure.

Specific Embodiment of the Sponge Counting Bag System with a Pail System The sponge counting bag embodiment just described for FIG. 1 is preferably used as attachable by adhesive means described therefor to the sheet 52 of FIG. 1C for example, along line 62 adjacent to the associated open end 58. Another embodiment of the present invention is shown in FIG. 1A whereby the multiple bag system described for FIGS. 5 and 6 is effectively draped from an extension of the pail support pole such that the lowest edge of the sponge counting bag system is held substantially above the rim of the pail 130 of FIG. 1A. This arrangement eliminates the need for the sponge counting bags preferably adhered to sheet 152 of FIG. 1C since the sponge counting function is achieved with a vertically accessible sponge counting bag system.

FIG. 1A further shows sponge counting bag pole support 200 which supports lower pole 201, height/rotation adjustment 202, and upper pole 204 such that sponge counting bag 50 hangs vertically above or just outside of the horizontal upper edge of pail 130. It is seen that sponges 209 may be deposited in sponge counting bag 50 by drawing open a bag section at flap 86. Sponge counting bag 50 is hung from holes 96 on hooks 205 which extend from wire frame 207. Wire frame 207 is supportively attached along horizontal extension 206 of upper pole 204. Wire frame 207 also may support documents related to sponge counting according the SpongTrak™ system.

Thus, according to this embodiment, routine deposition of used sponges may be made to a lined pail 130 during surgical procedures and the easily visible sponge counting bag 50 displays the results of subsequent counting and deposit of the sponges in pail 130 to the separate sections of sponge counting bag 130. This development provides at a glance from operating room personnel, even if located relatively far from the sponge counting bag 50, a quick visual check of the blood volume removed from a patient during surgery in the sponges. Since each of the bag sections of sponge counting bag 50 will contain a pre-determined number of sponges, i.e. five to 10, visual inspection of the number of sealed bag sections will quickly indicate by simple multiplication the approximate total number of sponges used and the degree of body fluid saturation in each one. It is a further advantage that the series of bag sections in sponge counting bag 50 provides a visual history of the progress of bodily fluid removal during the surgical procedure.

I claim:

1. A surgical sponge storage and counting system for use in a surgical operating room, comprising:
   a pail;
   a stand;
   a pail supporting member for supporting said pail;
   means for mounting said pail supporting member on said stand and for adjusting the height of said pail above the floor; and
   a bag member receivable in said pail for containing and storing used surgical sponges, the bag member further comprising a first sheet of flexible material forming a main bag having a periphery defining an open end of said main bag, a plurality of second bag members mounted to said first sheet and forming sponge holding bags mounted and spaced apart in a zone with annular proximity to the periphery, each second bag member having an upper open end, which faces away from the periphery and defines part of an inner edge of the zone with annular proximity to the periphery, and a lower closed end, which faces toward the periphery, the portion of the first sheet within the inner edge of the zone with annular proximity to the periphery adapted to be formed into a pail liner in a pail for receiving surgical sponges whereby the second bag members thereby hang at the outer sides of the pail with the upper open end above the lower closed end such that the second bag members may receive surgical sponges.

2. The bag member as defined in claim 1 wherein each said second bag member comprises a second sheet of flexible material forming a pocket and each said second sheet forms a flap for closing said pocket.

3. The bag member as defined in claim 1 wherein each of said second bag members has an open end which faces away from said periphery of said main bag.

4. The bag member as defined in claim 3 wherein each said second bag member comprises a second sheet of flexible material forming a pocket and each said second sheet forms a flap for closing said pocket.

* * * * *